(12) United States Patent
Weinzweig

(10) Patent No.: US 11,051,990 B2
(45) Date of Patent: Jul. 6, 2021

(54) SILICONE WOUND AND SCAR TREATMENT SYSTEM AND METHOD

(71) Applicant: Ashley Weinzweig, Highland Park, IL (US)

(72) Inventor: Ashley Weinzweig, Highland Park, IL (US)

( * ) Notice: Subject to any disclaimer, the term of this patent is extended or adjusted under 35 U.S.C. 154(b) by 417 days.

(21) Appl. No.: 16/006,323

(22) Filed: Jun. 12, 2018

(65) Prior Publication Data

US 2019/0029887 A1    Jan. 31, 2019

Related U.S. Application Data

(60) Provisional application No. 62/538,045, filed on Jul. 28, 2017, provisional application No. 62/636,537, filed on Feb. 28, 2018.

(51) Int. Cl.
| | | |
|---|---|---|
| *A61F 13/02* | (2006.01) | |
| *A61F 15/00* | (2006.01) | |
| *A61F 13/00* | (2006.01) | |

(52) U.S. Cl.
CPC ...... *A61F 13/0269* (2013.01); *A61F 13/0266* (2013.01); *A61F 15/002* (2013.01); *A61F 2013/00153* (2013.01); *A61F 2013/00217* (2013.01)

(58) Field of Classification Search
CPC .... A61F 15/002; A61F 15/001; A61F 15/004; A61F 15/005; A61F 15/006; A61F 15/007; A61F 13/0269; A61F 2013/00217; A61F 2013/0266; A61F 15/008; B65D 83/0805; B65D 83/672; B65D 5/0227
See application file for complete search history.

(56) References Cited

U.S. PATENT DOCUMENTS

| | | | | |
|---|---|---|---|---|
| 4,719,909 A * | 1/1988 | Micchia | ................. | A45D 44/00 128/858 |
| 2005/0178783 A1* | 8/2005 | Pastan | ................... | A61B 50/10 221/58 |
| 2012/0292426 A1* | 11/2012 | Arefieg | .................... | B26D 3/02 242/590 |
| 2015/0238376 A1* | 8/2015 | Seibold | ................. | A61F 15/002 221/73 |
| 2016/0113818 A1* | 4/2016 | Rovaniemi | ....... | A61F 13/00038 607/47 |
| 2016/0135999 A1* | 5/2016 | Mikoll | .................. | A61F 15/006 602/57 |
| 2020/0281783 A1* | 9/2020 | Al-Sulaimani | ...... | B65H 54/585 |

* cited by examiner

*Primary Examiner* — Alireza Nia
*Assistant Examiner* — Daniel A Miller
(74) *Attorney, Agent, or Firm* — Saul Ewing Arnstein & Lehr LLP

(57) ABSTRACT

The present invention relates to a dispenser for the silicone sheeting and the adhesive anchors and method for treating sites, such as wounds or closed incisions, using the silicone sheeting and anchors. The silicone sheeting may be provided in the form of a roll, which includes a leader. The silicone sheeting may be cut from the roll, or may be of precut sizes. Adhesive anchors may be cut from a roll or may be of precut sizes. The dispenser allows for easy access to silicone sheeting for wound treatment and adhesive anchors for securement of the silicone sheets, especially in high tension areas of the body.

7 Claims, 7 Drawing Sheets

SILICONE WOUND AND SCAR TREATMENT SYSTEM AND METHOD

FIELD OF THE INVENTION

The present invention relates to a system and method for treating wounds and closed incisions from surgical procedures.

BACKGROUND OF THE INVENTION

Healing from wounds and prevention of scarring, such as from incisions encountered during surgical procedures, quickly and safely are important to the treatment process. Commonly used to protect wounds and closed incisions from contamination are dressing such as fabric bandages. A drawback of such dressings is that during removal of the dressing, the fabric may stick to the tissue and reopen the wound.

In some instances, silicone dressings are used to cover a wound or closed incision to aid in healing. Such silicone dressings are dressings coated with soft silicone as an adhesive or a wound contact layer. The intrinsic properties of soft silicone are such that these dressings may be removed without causing trauma to the wound, closed incision, or to surrounding skin. Published studies suggest that patients whose wounds or closed incisions are dressed with soft silicone dressings experience less trauma, less discomfort on removal and less maceration than those dressed with conventional dressings, thus reducing treatment costs.

As discussed, a benefit of silicone dressings is that it will not stick to the wound or closed incision, or cause trauma to the treatment site when removed. However, this benefit also results in a shortcoming of silicone dressings that has not been addressed due to the generally poor adherence of the dressing to the patient's skin. This is especially the case with incisions in certain places on the body that are prone to causing high tension areas on the dressing, such as a shoulder, elbow or knee. It is sometimes the case that the silicone dressing will release from the patient's skin.

SUMMARY OF THE INVENTION

For wound or post-surgical closed incision treatment, a silicone sheet may be applied directly over a wound or an incision site. The silicone sheet may be provided with a backing, which, when removed, exposes an adhesive layer. In order to better secure the silicone sheet to the site, adhesive anchors may be applied over a portion of the silicone sheet when the silicone sheet is positioned in place. For example, in the example of a surgical procedure in the shoulder area, the silicone sheet section may be placed over the site, an adhesive anchor may be placed at one end of the silicone sheet section, and then a second adhesive anchor placed over a portion of the silicone sheet between the ends, and particularly in a higher tension area, and a third adhesive anchor placed over a second end portion of the silicone sheet section.

Some aspects of the present invention relate to a dispenser for the silicone sheeting and the adhesive anchors. The dispenser provides several advantages. The silicone sheeting is provided in the form of a roll, which includes a leader, which is preferably made of a foil material. The leader allows for easier dispensing of the silicone sheeting. The silicone sheeting may be cut from the roll by way of a scissors or other separate cutting implement, or may be cut with a cutting surface integral with the dispenser. Another advantage relates to selectable displays, such as for displaying UPC codes. Different jurisdictions often have different labelling standards. In many instances this requires suppliers to either have different printed boxes for different jurisdictions, or create separate labels to affix to packaging for different jurisdictions.

According to a preferred embodiment of the present invention, the wound or closed incision treatment system comprises a dressing dispenser unit and an adhesive anchor dispensing unit. With each of the dressing dispenser unit and the adhesive anchor dispensing unit, the dispensing units include a case that defines an interior. The case also defines an aperture through which the supply of silicone dressings or adhesive anchors is drawn. The silicone dressings are removably secured to a dressing backing ribbon. The adhesive anchors are also removably secured to an anchor backing ribbon. Each of the dressing backing ribbon and the anchor ribbon is preferably wrapped around its respective barrel member. Each barrel member may, in some embodiments, be mounted within either the dressing dispenser unit or anchor dispensing unit on a spindle that extends across opposed sidewalls thereof. The adhesive anchors are preferably precut into a desired shape or shapes. For example, anchors that are butterfly shaped may be preferred to secure certain areas, whereas, elongated shapes may be preferred in others. Fanciful or decorative shaped anchor members can also be used, such as diamonds, crescents, footballs, clover leafs, or the like. It may also be desirable to include graphic designs on the anchors to provide some aesthetic benefits and whimsy.

Each of the dressing backing ribbon and anchor ribbon may include a leader portion. The leader portion of the dressing backing ribbon is preferably extended through the dressing aperture and held by a dressing loop formed on the exterior of the dressing dispensing unit. Similarly, the leader portion of the anchor ribbon is preferably extended through the anchor ribbon aperture and held by an anchor loop formed on the exterior of the anchor dispensing unit.

The dispenser unit case for either or both of the silicone dressing and the adhesive anchors may preferably include a plurality of sides defining an open end and a closure system for closing the open end. The closure system preferably includes a first flap member configured to occlude the open end. The first flap member may be hinged with the body about the open end. The first flap member also includes a tab member. A second flap member is also provided. This second flap member is also configured to occlude the open end, may be hinged with the body about the open end, and may include a tab member. Formed proximate the open end is a first slot and a second slot. In some embodiments, the first slot member may be formed in the second flap member or adjacent thereto, and the second slot member may be formed in the first flap member or adjacent thereto. The first tab is adapted to be received in the second slot, and the second tab is adapted to be received in the first slot. Since either of the first flap member or second member may close the open end, different printing may be placed on the exterior portions of the first and second flap members, respectively, such that a single printing run can incorporate different visible markings, if desired. For example, different jurisdictions may have different labeling requirements. By having a single printed box be adaptable to displaying different markings, a suppler is able to reduce packaging inventories.

In another embodiment, it may be desirable to have a single dispensing unit for both the silicone dressings and the anchors. In such an embodiment, the dispenser unit defines an interior, a silicone dressing aperture, and an adhesive anchor aperture. As with the previous embodiment, a dressing backing ribbon including a plurality of silicone dressings removably secured thereto is provided, and the dressing aperture is sized to allow a portion of the dressing backing ribbon to exit the dispenser unit. Also, an adhesive anchor backing ribbon is provided that includes a plurality of adhesive anchors, where each anchor having an adhesive backing and removably secured to the adhesive anchor backing ribbon. The adhesive anchor aperture is sized to allow a portion of the adhesive anchor backing ribbon to exit the dispenser unit.

In this embodiment, the dispenser unit includes a dressing loop formed on the exterior thereof that is aligned with the dressing aperture, and an anchor loop formed on the exterior thereof that is aligned with the anchor aperture. The dressing backing ribbon includes a leader portion, and the dressing loop is adapted to receive the leader portion of the dressing backing ribbon, and the adhesive anchor backing ribbon includes a leader portion, which is adapted to be received in the anchor loop.

In this embodiment, a dressing barrel member and an anchor barrel member, each defining an outer surface and an interior passage are provided. The dressing ribbon and the anchor ribbon are wrapped around the outer surface of their respective barrel, and the barrels are rotatably mounted on a spindle. A closure system may be provided similar to the closure system for the individual dressing dispensing unit or anchor dispensing unit.

The present invention may also include a drying system. Pieces of silicone sheeting may be washed and reused. A rack may be provided for drying the silicone sheeting.

According to a preferred method of using the silicone sheeting, a silicone sheet removed from the dressing ribbon and placed over a wound. For sake of example, an incision to a shoulder is discussed, because this is a high movement, high stress area for wound recovery. The silicone dressing is placed over the wound. If necessary, multiple dressings can be used. Anchor members may then be removed from the anchor ribbon. These are preferably placed at the ends of the silicone sheet and secured to the patient's skin. Additional anchors are placed at points along the silicone sheet, and particularly in high stress areas. In some embodiments, the anchors are formed of a stretchable material such that strain on the anchors is absorbed by stretch, such that they continue to adhere to the patient's skin and silicone sheet. The position of the silicone sheet between the adhesive anchor and the wound area prevents any trauma to the wound area.

BRIEF DESCRIPTION OF THE DRAWINGS

Illustrative, non-limiting embodiments are shown in the drawings, in which.

DETAILED DESCRIPTION OF EMBODIMENTS

Preferred embodiments of the claimed silicone wound treatment system and method are hereunder described with reference to the attached drawings.

Figure 1:
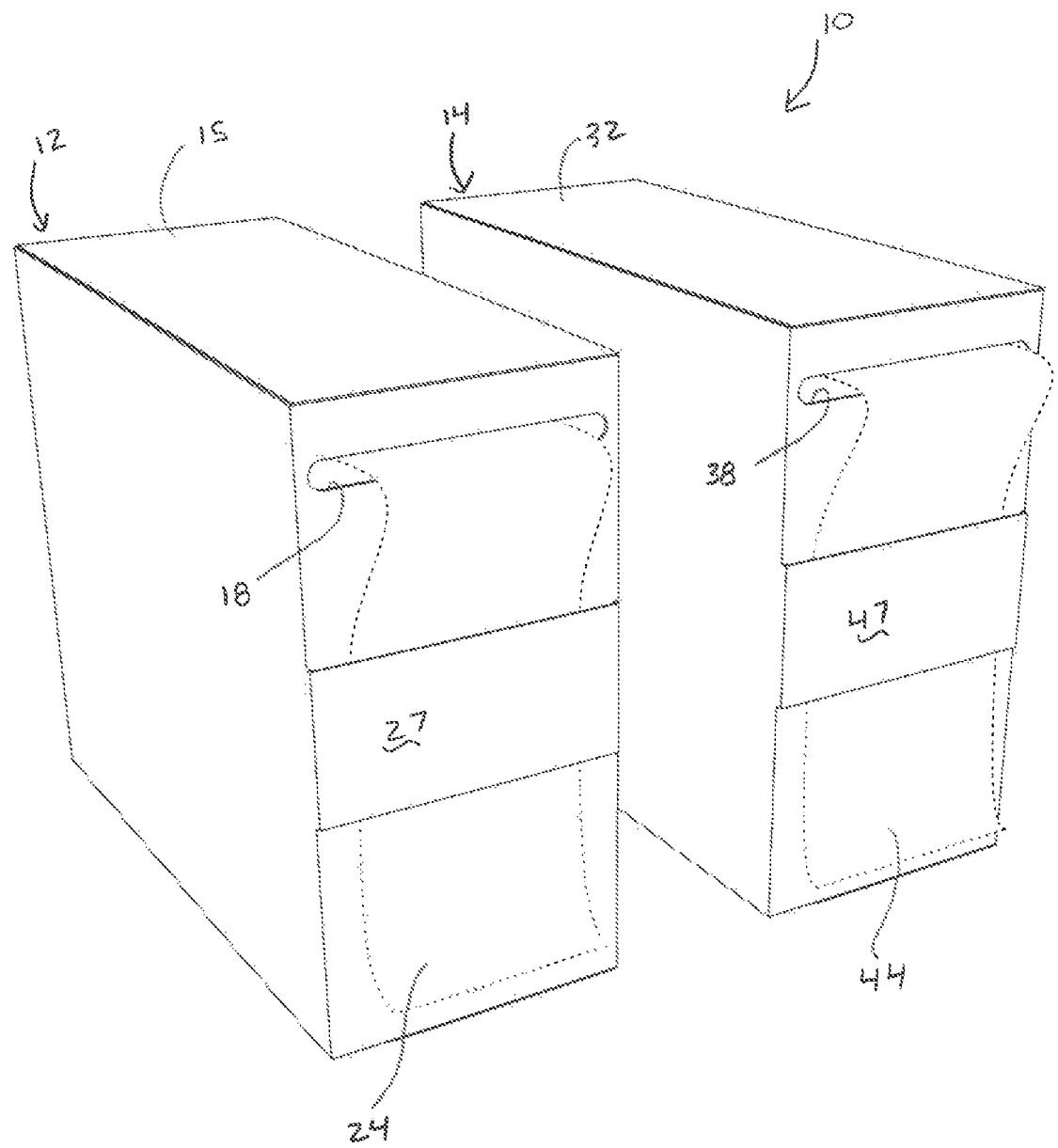
FIG. 1 illustrates a perspective view of a preferred embodiment of the present invention.
Figure 2:
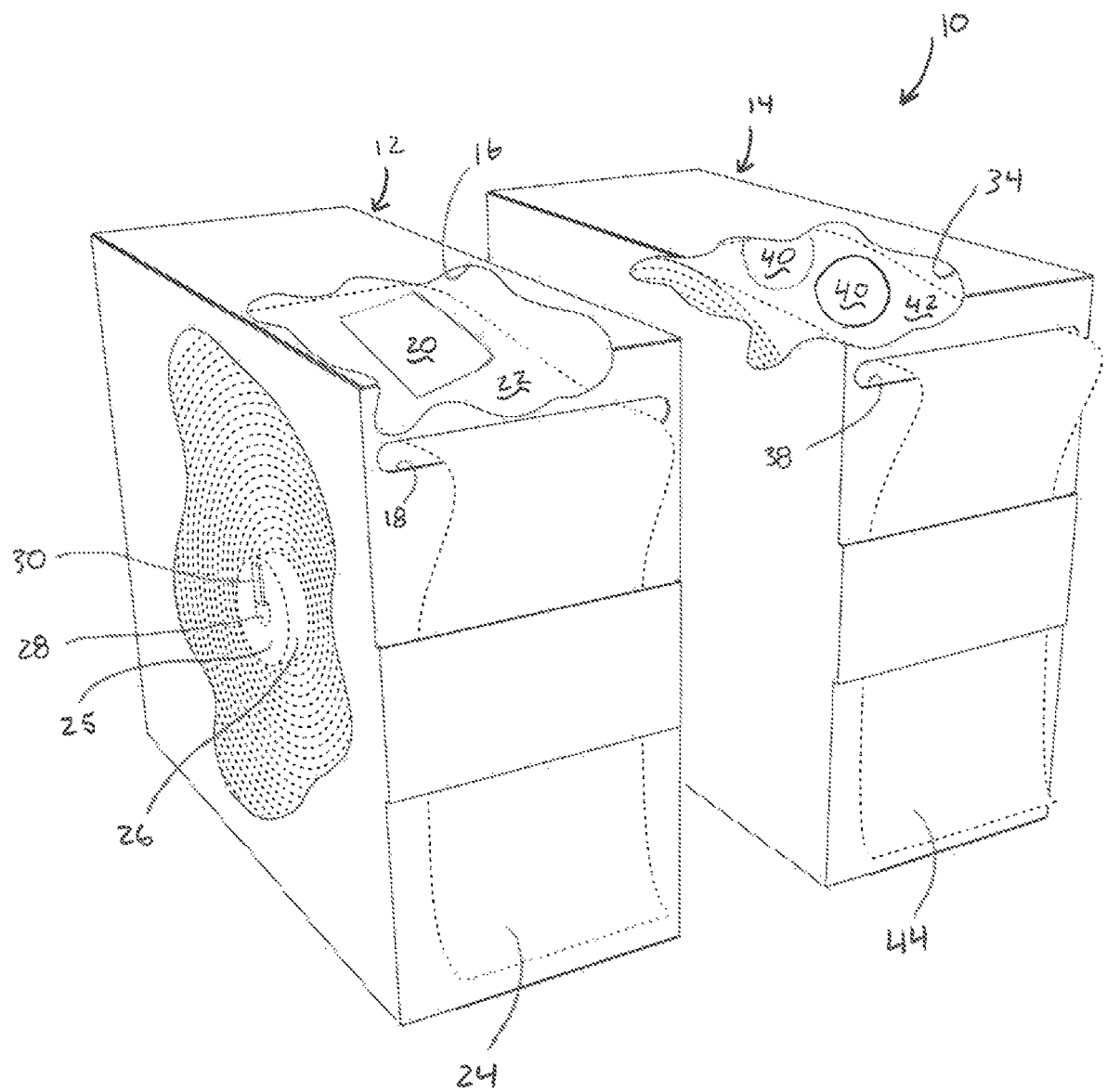
FIG. 2 illustrates a perspective view of a preferred embodiment of a dressing dispensing unit and an adhesive anchor dispensing unit, each with a portion cutaway to illustrate their respective interiors.

Referring to FIGS. 1 and 2, a treatment system 10 according a preferred embodiment of the invention is described. The system 10 includes a dressing dispenser unit 12 and an adhesive anchor dispensing unit 14. The dressing dispenser unit 12 includes a case 15. As shown in FIG. 2, the case 15 defines an interior 16. Formed in one of the walls of case 15 is an aperture 18 through which the supply of silicone dressings may be drawn. The silicone dressings 20 are removably secured to a dressing backing ribbon 22. The dressing backing ribbon 22 may also include a leader portion 24. The dressing backing ribbon 22 may be wound on a barrel member 25. The barrel member 25 includes an exterior portion 26 upon which the ribbon 22 is wound. The barrel member may also include a through passage 28. In some embodiments, the dressing dispensing unit 12 may include a support 30. The passage 28 is configured to receive the support 30. Although not shown, it should be understood that the support would be connected to the wall of case 15 such that the backing ribbon 22 and silicone dressings 20 thereon are supported. Formed on an exterior of the case 15 in an aligned relationship with aperture 18 is a loop 27. Leader 24 and portions of the dressing backing ribbon 22 that are pulled from the dispenser 12 are guided through loop 27.

The anchor dispenser unit 14 is similar in most respects to the dressing dispenser unit 12. The anchor dispenser unit 14 includes a case 32, and defines an interior 34. Formed in one of the walls of case 32 is an aperture 38 through which the supply of adhesive anchors may be drawn. The adhesive anchors 40 are removably secured to an anchor backing ribbon 42. The anchor backing ribbon 42 may also include a leader portion 44. The anchor backing ribbon 42 may be wound on a barrel member in a similar manner to the silicone dressing barrel 25. As with the dressing dispenser unit 12, formed on an exterior of the case 32 of the anchor dispenser unit 14 in an aligned relationship with aperture 38 is a loop 47. Leader 44 and portions of the dressing backing ribbon 42 that are pulled from the dispenser 14 are guided through loop 47. Although not shown, each of the dispenser units 12 and 14 may include a blade, serrated edge, or other cut off feature to cut off excess backing ribbon. The loops may be of any shape, and need not be round, arcuate, or circular.

Figure 3:
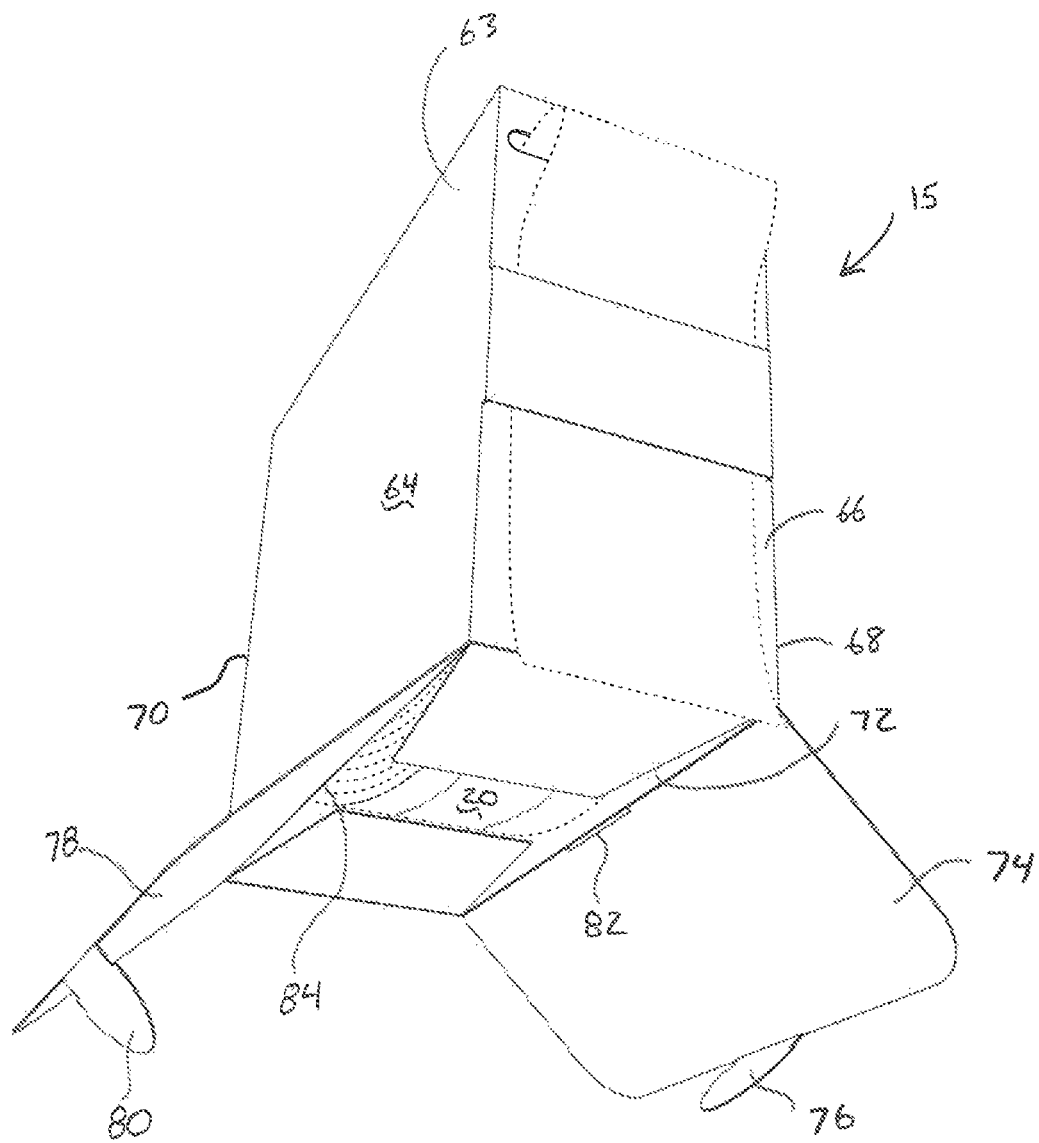
FIG. 3 illustrates a perspective view of a closure system.
Figure 4:
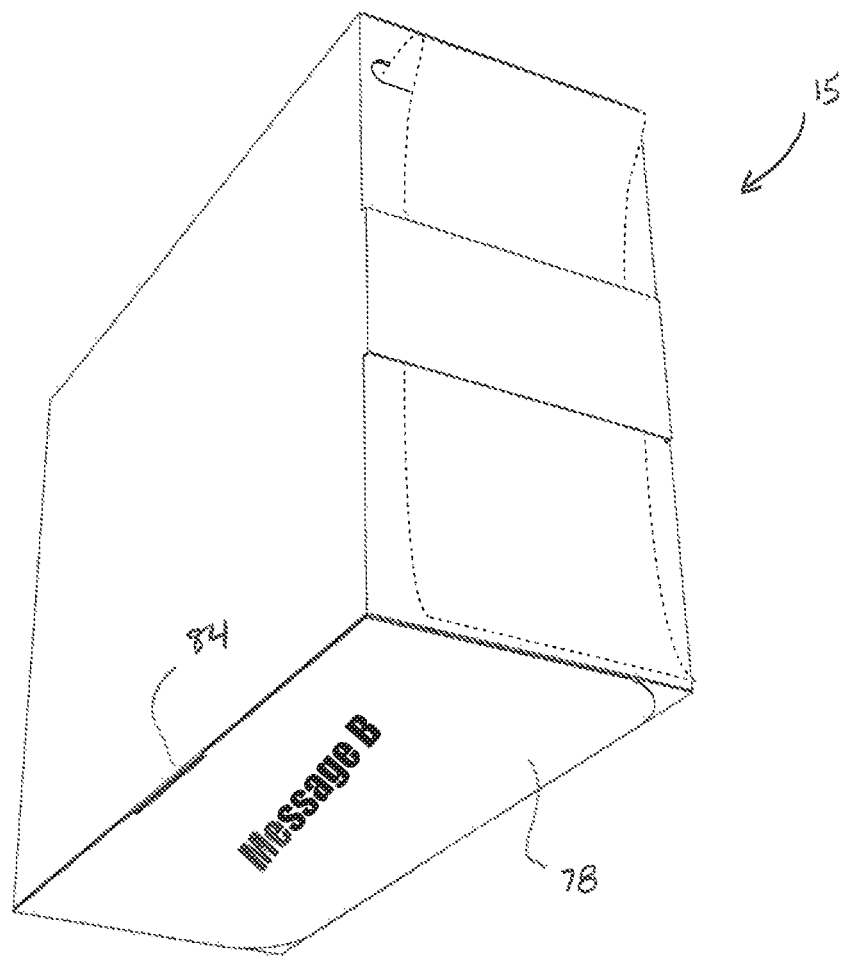
FIG. 4 is a perspective view of a dispensing unit depicting the closure system in a closed position.
Figure 5:
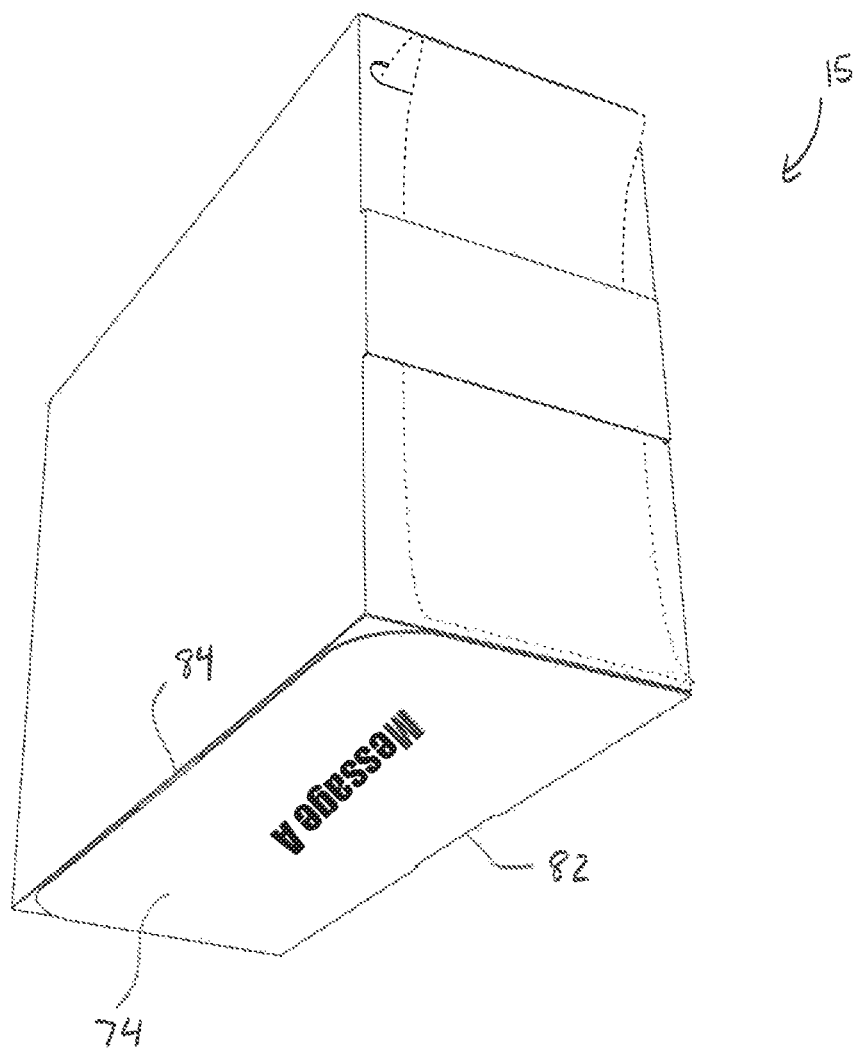
FIG. 5 is a perspective view of a dispensing unit depicting the closure system in an alternate closed position.

Referring to FIGS. 3-5, each of the dressing dispenser unit case 15 and the anchor dispensing unit case 32 may include a closure system. For sake of reference, dressing dispenser unit case 15 is shown. The dressing dispenser unit case 15 includes a body 63 that includes a plurality of sides 64, 66, 68, 70, which collectively define an open end 72. The closure system preferably includes a first flap member 74 which is sized to occlude or close the open end 72. The first flap member 74 may be hinged with the body 63 about the open end 72. The first flap member 74 also includes a first tab 76. A second flap member 78 may also be provided. This second flap member 78 is preferably positioned on the opposite side of open end 72 to the first flap member 74, and is also configured to occlude or close the open end 72. As with the first flap member, second flap member may be hinged with the body 63 about the open end 72, and may include a second tab 80. Formed proximate the open end is a first slot 82 and a second slot 84. In some embodiments, the first slot 82 may be formed in the second flap member 78 or adjacent thereto, and the second slot 84 may be formed in the first flap member 74 or adjacent thereto. The first tab 76 is adapted to be received in the second slot, and secured therein. Similarly, the second tab 80 is adapted to be received and secured in the first slot 82. Since either of the first flap member or second member may close the open end, different printing, such as "Message A" and "Message B," may be placed on the exterior portions of the first and second flap members, respectively, such that a single printing run can incorporate different visible markings, such as shown in FIGS. 4 and 5.

Figure 6:
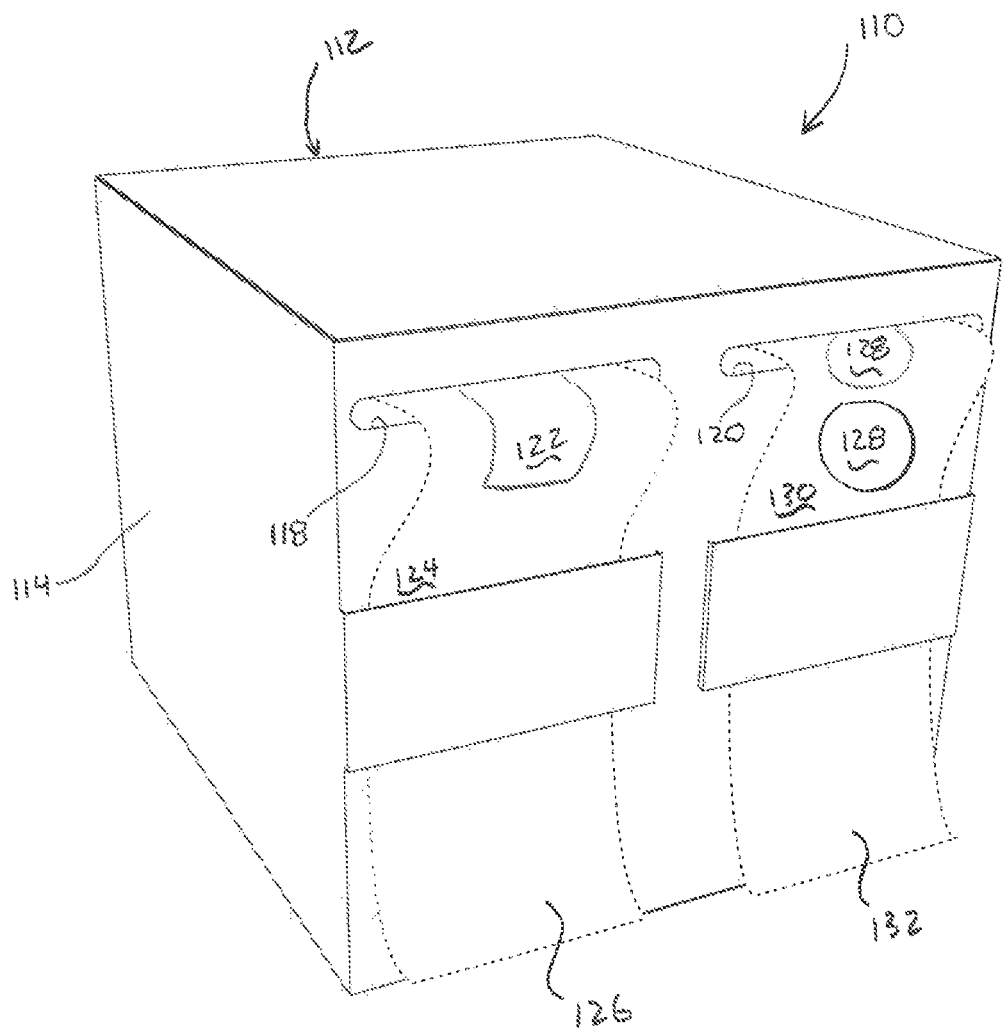
FIG. 6 is a perspective view of an alternative dispensing unit.

Referring to FIG. 6, an alternate embodiment is shown. In this embodiment, wound treatment system 110 includes a dispenser unit 112 for both silicone dressing and adhesive anchors. The dressing dispenser unit 112 includes a case 114. The case 114 defines an interior (not shown). Formed in one of the walls of case 114 are apertures 118 and 120 through which the supply of silicone dressings and the supply of adhesive anchors may be drawn. Although shown as being formed in the same wall, the apertures 118 and 120 may be formed in different walls. Also, it is contemplated that multiple rolls of dressings and anchors, perhaps of different sizes and shapes, can be included in a single dispensing unit. As before, the silicone dressings 122 are removably secured to a dressing backing ribbon 124, which may include leader portion 126, and the adhesive anchors 128 are removably secured to an anchor backing ribbon 130, which may include leader portion 132. Although not shown in detail in the drawings it should be recognized that the closure system discussed above can be included in the dispenser unit 112.

Figure 7:
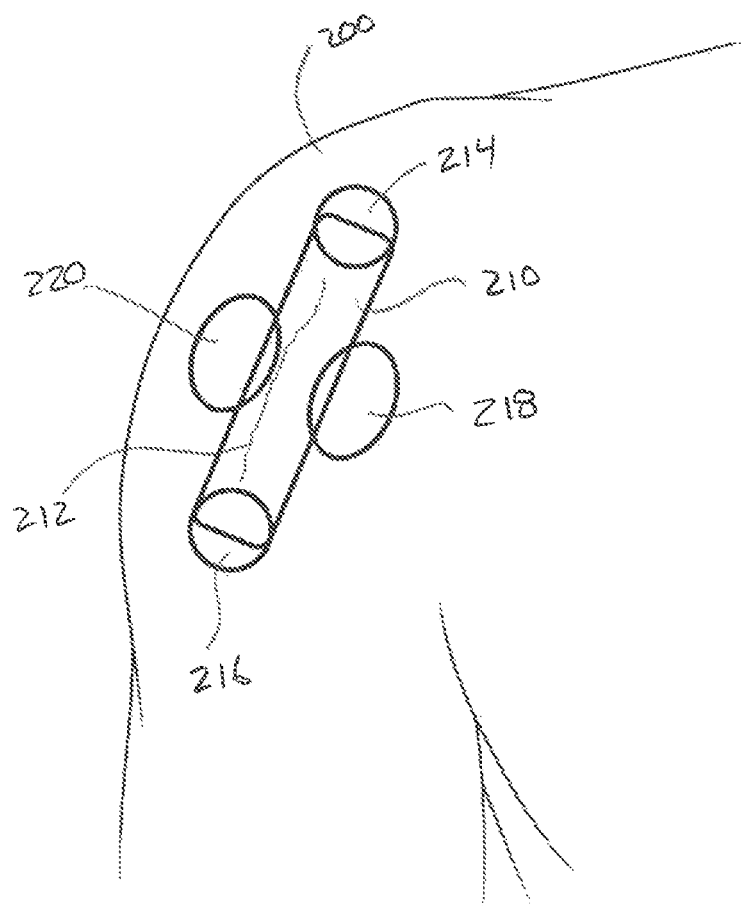
FIG. 7 is a perspective view of a schematic of a shoulder depicting an exemplary use of the wound treatment system.

An exemplary method of using the silicone sheeting is shown with respect to FIG. 7. A schematic of a shoulder 200 is shown. A silicone sheet 210, which has been removed from the dressing ribbon, is placed over a wound, such as incision 212. Anchor members 214 and 216, which have been removed from the anchor ribbon are then placed at the ends of the silicone sheet and secured to the patient's skin. Additional anchors, such as anchors 218 and 220 are placed at points along the silicone sheet in high stress areas. In so doing, the silicone sheet is secured with the patient to allow the wound to heal and reduce scarring.

Although only a few embodiments of the present inventions have been described in detail in this disclosure, those skilled in the art who review this disclosure will readily appreciate that many modifications are possible without materially departing from the novel teachings and advantages of the subject matter recited herein.

I claim:

1. A treatment system comprising:
  a dressing dispenser unit, the dressing dispenser unit including a dressing case defining an interior, said dressing case further defining an aperture;
  a dressing backing ribbon including a plurality of silicone dressings removably secured thereto, said aperture sized to allow a portion of the dressing backing ribbon to exit the dressing case;
  an adhesive anchor dispenser unit, the adhesive anchor dispenser unit including an adhesive anchor case defining an interior, said adhesive anchor case further defining an aperture;
  an adhesive anchor backing ribbon including a plurality of anchors, each anchor having an adhesive backing and removably secured to the adhesive anchor backing ribbon; and
  wherein at least one of the dressing dispenser unit case or the adhesive anchor dispenser unit case defines a body including a plurality of sides defining an open end, the at least one of the dressing dispenser unit case or the adhesive anchor dispenser unit case further including a closure system for closing the open end, the closure system including:
  a first flap member hinged with the body about the open end and having a first tab, the first flap member configured to occlude the open end,
  a second flap member hinged with the body about the open end and having a second tab, the second flap member configured to occlude the open end,
  a first slot proximate the open end adapted to receive the second tab, and
  a second slot adapted to receive the second tab adapted to receive the first tab.

2. The treatment system of claim 1,
  wherein the dressing backing ribbon includes a leader portion, and the dressing case having formed with an exterior thereof a loop adapted to receive the leader portion of the dressing backing ribbon and the dressing backing ribbon; and
  wherein the adhesive anchor backing ribbon includes a leader portion, and the adhesive anchor case having formed with an exterior thereof a loop adapted to receive the leader portion of the adhesive anchor backing ribbon and the adhesive anchor backing ribbon.

3. The treatment system of claim 1,
  the dressing dispenser unit case including opposed sidewall members and a support bridging the opposed sidewall members;
  a barrel member defining an outer surface and an interior passage, the dressing backing ribbon being wrapped around the outer surface of the barrel member, and the interior passage adapted to receive the support such that the dressing backing ribbon is rotatably mountable on the support.

4. The treatment system of claim 1,
  the adhesive anchor dispenser unit case including opposed sidewall members and a support bridging the opposed sidewall members;
  a barrel member defining an outer surface and an interior passage, the adhesive anchor backing ribbon being wrapped around the outer surface of the barrel member, and the interior passage adapted to receive the support such that the adhesive anchor backing ribbon is rotatably mountable on the support.

5. A treatment system comprising:
  a dispenser unit defining an interior, said dispenser unit further defining a silicone dressing aperture and an adhesive anchor aperture;
  a dressing backing ribbon including a plurality of silicone dressings removably secured thereto, the dressing aperture sized to allow a portion of the dressing backing ribbon to exit the dispenser unit;
  an adhesive anchor backing ribbon including a plurality of adhesive anchors, each anchor having an adhesive backing and removably secured to the adhesive anchor backing ribbon, the adhesive anchor aperture sized to allow a portion of the adhesive anchor backing ribbon to exit the dispenser unit;
  wherein the dispenser unit includes opposed sidewall members and a spindle bridging the opposed sidewall members;

a dressing barrel member defining an outer surface and an interior passage, the dressing backing ribbon being wrapped around the outer surface of the barrel member;

an anchor barrel member defining an outer surface and an anchor interior passage, the adhesive anchor backing ribbon being wrapped around the outer surface of the anchor barrel member, and the anchor interior passage adapted to receive the spindle such that the adhesive anchor backing ribbon is rotatably mountable on the spindle; and wherein the dispenser unit defines a body including a plurality of sides defining an open end, and further includes a closure system for closing the open end, the closure system including:

a first flap member hinged with the body about the open end and having a first tab, the first flap member configured to occlude the open end, a second flap member hinged with the body about the open end and having a second tab, the second flap member configured to occlude the open end, a first slot proximate the open end adapted to receive the second tab, and a second slot adapted to receive the second tab adapted to receive the first tab.

6. The treatment system of claim 5, wherein:

the dispenser unit includes a dressing loop formed on the exterior thereof and aligned with the dressing aperture and an anchor loop formed on the exterior thereof and aligned with the anchor aperture;

the dressing backing ribbon includes a leader portion, and the dressing loop is adapted to receive the leader portion of the dressing backing ribbon; and the adhesive anchor backing ribbon includes a leader portion, and the anchor loop is adapted to receive the leader portion of the anchor backing ribbon.

7. The treatment system of claim 5 further comprising a silicone dressing drying rack.

* * * * *